United States Patent
Marcovici et al.

[11] Patent Number: 5,991,357
[45] Date of Patent: Nov. 23, 1999

[54] INTEGRATED RADIATION DETECTING AND COLLIMATING ASSEMBLY FOR X-RAY TOMOGRAPHY SYSTEM

[75] Inventors: Sorin Marcovici, Lexington; Simon George Harootian, Worcester; Ben Tuval, Brookline, all of Mass.

[73] Assignee: Analogic Corporation, Peabody, Mass.

[21] Appl. No.: 08/991,852

[22] Filed: Dec. 16, 1997

[51] Int. Cl.⁶ .................................................... G01T 1/20
[52] U.S. Cl. .......................... 378/19; 378/149; 378/154; 250/370.09
[58] Field of Search ............................ 378/19, 4, 7, 147, 378/149, 154; 250/370.09, 363.01, 363.02, 363.08, 367

[56] References Cited

U.S. PATENT DOCUMENTS

| | | |
|---|---|---|
| 4,338,521 | 7/1982 | Shaw et al. .............................. 250/366 |
| 4,429,227 | 1/1984 | DiBianca et al. ........................ 250/367 |
| 4,845,363 | 7/1989 | Akai ......................................... 250/368 |
| 4,982,096 | 1/1991 | Fujii et al. ............................... 250/367 |
| 5,487,098 | 1/1996 | Dobbs et al. .............................. 378/19 |
| 5,781,606 | 7/1998 | Dobbs et al. .............................. 378/19 |
| 5,799,057 | 8/1998 | Hoffman et al. ........................ 378/147 |
| 5,841,829 | 11/1998 | Dolazza et al. ............................. 378/4 |

*Primary Examiner*—David P. Porta
*Assistant Examiner*—Drew A. Dunn
*Attorney, Agent, or Firm*—Lappin & Kusmer LLPL

[57] ABSTRACT

An integrated radiation detecting and collimating assembly for an x-ray tomography scanning system. The assembly includes a housing which mounts to a spine of the system and aligns corresponding arrays of photodiodes, scintillator crystals and anti-scatter plates with one another and with x-ray beams arriving directly at the detectors from the focal spot. The arrays of photodiodes, crystals and anti-scatter plates are thus all fixed relative to one another within the housing, which is itself securely fixed to the frame of the scanner system.

16 Claims, 3 Drawing Sheets

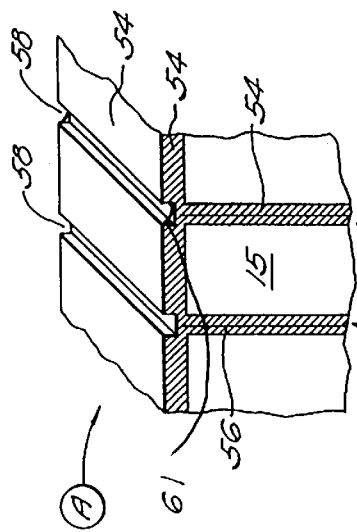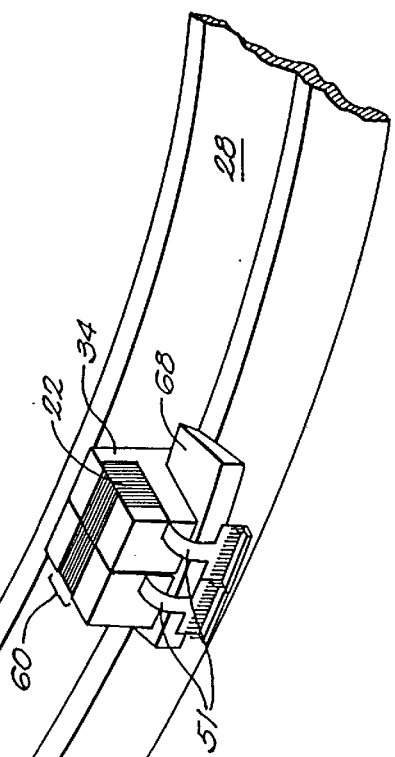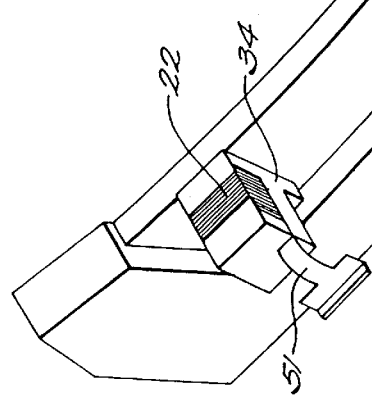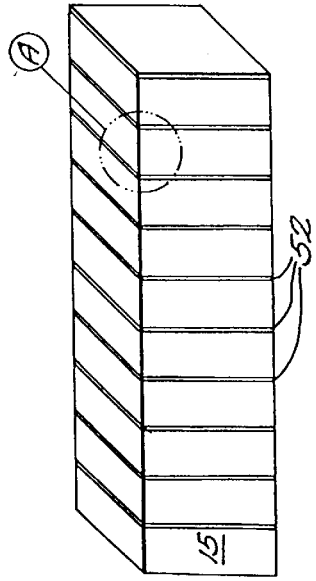

INTEGRATED RADIATION DETECTING AND COLLIMATING ASSEMBLY FOR X-RAY TOMOGRAPHY SYSTEM

TECHNICAL FIELD

The present invention relates to radiation detector systems for x-ray computed tomography (CT) systems, and more particularly to modular arrangements of radiation detectors and related components.

BACKGROUND OF THE INVENTION

CAT scanners of the third-generation type include an X-ray source and X-ray detector system secured respectively on diametrically opposite sides of an annular disk. The latter is rotatably mounted within a gantry support so that during a scan the disk rotates about a rotation axis while X-rays pass from the source through an object positioned within the opening of the disk to the detector system.

The detector system typically includes an array of detectors disposed as a single row along an arc of a circle having a center of curvature at the point, referred to as the "focal spot," from which the radiation emanates from the X-ray source. The X-ray source and array of detectors are all positioned so that the X-ray paths between the source and each detector all lie in the same plane (hereinafter the "rotation plane" or "scanning plane") normal to the rotation axis of the disk. Because the ray paths originate from substantially a point source and extend at different angles to the detectors, the ray paths resemble a fan, and thus the term "fan beam" is frequently used to describe all of the ray paths at any one instant of time. The X-rays that are detected by a single detector at a measuring instant during a scan are hereinafter referred to as a "ray." The ray is partially attenuated by the mass of all objects in its path so as to generate a single intensity measurement as a function of the attenuation, and thus the density, of the mass in that path. Projections, i.e., the X-ray intensity measurements, are typically done at each of a plurality of angular positions of the disk.

An image reconstructed from data acquired at all of the projection angles during the scan will be a slice along the scanning plane through the object being scanned. In order to reconstruct a density image of the section in a defined rotation plane, the image is typically reconstructed in a pixel array, wherein each pixel in the array is attributed a value calculated from the attenuation of all of the rays that pass through it during a scan. As the source and detectors rotate around the object, rays penetrate the object from different directions, or projection angles, passing through different combinations of pixel locations. The density distribution of the object in the slice plane is mathematically generated from these measurements, and the brightness value of each pixel is set to represent that distribution. The result is an array of pixels of differing values which represents a density image of the scanning plane.

In order for the image reconstruction process to work, the position of the rays must be precisely known. In order to accurately position the rays without an unmanageable amount of calibration and correction, it is therefore very useful to have accurately located detectors, and measurements accurately timed so that the angular position of each detector for each projection is predetermined.

Further, since dense matter tends to scatter X-rays, it is important that any radiation that does not traverse a straight line from the source to each detector be excluded from the measurements by each such detector. To remove this scattered radiation, a series of very thin anti-scatter plates is typically inserted between the detectors and the object with the individual plates aligned so as to collimate the rays from the radiation source by allowing to pass to the detectors substantially only those rays traversing a straight, radial line between the source and each detector.

Unfortunately, the need for the anti-scatter plates creates additional difficulties because if they cast an X-ray "shadow" on a detector, they will interfere with its measurements. Not only will the output of each shadowed detector be reduced, but it will also be modulated by the least vibration or lateral movement of the source, anti-scatter plates and/or detectors.

The difficulty of meeting these requirements becomes evident when one considers that in order to provide the kind of resolution expected of modern X-ray tomographic scanners, the detectors number in the hundreds with several detectors located within a single degree of the fan beam arc. This makes the width of a typical detector on the order of a millimeter, and the dimensions of a typical anti-scatter plate about 20 mm long in the radial direction by about 0.1 mm thick, requiring extremely accurate detector and anti-scatter plate location and alignment. To further compound the problem, the whole assembly is usually rotated around the scanned object at a rate of about 60 to 120 rpm, generating substantial varying forces and requiring rugged mounting techniques.

Previous attempts to satisfy these difficult requirements have produced machines of very large mass, requiring very costly, painstaking assembly techniques with a great deal of effort spent in alignment of the anti-scatter plates and detectors. If for any reason one or more elements has to be replaced or realigned, the reassembly and realignment process is usually too demanding to be performed in the field, and the entire detector subsystem often has to be returned to the factory.

One approach to this problem is to establish preassembled modules for the detector and anti-scatter plate arrays, as disclosed in, for example, U.S. Pat. No. 5,487,098 to Dobbs et al., assigned to the assignee of the present invention. The detector and anti-scatter plate modules must each be attached to a support structure or spine which must then be attached to a rotating gantry of the tomography system. Each detector module therefore must be aligned with a corresponding anti-scatter plate module, and each pair of modules must be aligned relative to the focal spot in order to maximize receipt of radiation.

Another approach is disclosed in U.S. Pat. No. 4,338,521 to Shaw et al., in which a modular detector array includes two detachably assembled portions, one containing the detectors and the other containing the anti-scatter plates. The two portions of the array must be assembled together in order to establish their mutual alignment. The assembled module must then be aligned with the radiation source and then fixedly mounted to the tomography apparatus.

A difficulty with high-resolution detector subsystems is obtaining and maintaining the relatively tight alignment requirements of the detectors and anti-scatter plates with the x-ray beams from the radiation source. Tolerances are further strained by any temperature and vibrational changes in the relative alignment of the subsystems.

OBJECTS OF THE INVENTION

It is an object of the present invention to obviate the disadvantages of the prior art.

It is a further object of the invention to provide a radiation detection system for a computed tomography scanner which substantially eliminates the tedious alignments of individual detector modules with corresponding anti-scatter plate modules, and the alignments of these pairs of modules with the radiation source.

It is another object of the invention to provide an integrated structure for a radiation detection system which maximizes radiation detection and simplifies the construction, assembly and maintenance of the tomography apparatus.

SUMMARY OF THE INVENTION

The present invention provides an integrated, modular assembly which incorporates and mutually aligns a radiation detector assembly and a radiation collimation assembly. The integrated assembly also includes a beam collimator structure which collimates or channels the x-ray beams after passage through the object being scanned and prior to passage through the anti-scatter plates and impingement on the detectors. This integrated construction eliminates the tedious alignment of individual detector arrays with individual anti-scatter plate arrays and the alignment of each of these arrays with their respective support structures, which must themselves be aligned with the focal spot and mounted on the rotating gantry of the tomography system.

According to the invention, there is provided an integrated radiation detecting and collimating assembly for an x-ray tomography system. The tomography system includes a source of radiation, means for supporting an object to be scanned, means for detecting radiation passing through the object and for providing electrical signals representative of the relative attenuation of portions of the object, and a frame for rotatably supporting the radiation source and the detecting means relative to the object. The integrated radiation detecting and collimating assembly comprises:

a. A plurality of photodiodes arranged in an array on a substrate;

b. A plurality of scintillator crystals arranged to receive x-rays from the radiation source, each of the crystals being spaced from one another by a substantially non-detecting region and each crystal being arranged in a corresponding array and aligned and optically coupled with a corresponding photodiode;

c. A plurality of anti-scatter plates arranged over the crystals in a substantially linear array, each plate being aligned with a corresponding non-detecting region between adjacent crystals; and d. A housing for the assembly, comprising a central support section for supporting the substrate so that the scintillator crystals are exposed to x-rays from the radiation source, and a pair of walls extending from the central support section to define an interior region for the photodiode, crystal and anti-scatter plate arrays, and means for passage of electrical connections from the photodiodes through the housing to a data acquisition system. The photodiodes, scintillator crystals and anti-scatter plates are thus all fixed relative to one another within the housing. The housing is adapted for secure fixation to the frame.

The integrated assembly can further include an x-ray collimation structure extending from the walls of the housing to define a radiation collimation region for receiving and collimating x-rays entering the housing after passage through the object being scanned. The x-ray collimation structure includes a pair of x-ray opaque collimator support plates, and means for aligning and securing the anti-scatter plates between the collimator support plates.

In one embodiment, the x-ray opaque collimator support plates are formed from integral extensions of the housing walls and include an x-ray opaque covering over a pair of non-x-ray opaque support structures. In another embodiment, the collimator support plates comprise separate x-ray opaque plates which are fixedly attached to the housing walls.

In a preferred embodiment, the means for aligning and securing the anti-scatter plates between the collimation plates comprises a plurality of alignment slots in each of the collimation plates. Corresponding alignment slots are aligned with each other and are adapted to engage corresponding vertical edges of an anti-scatter plate therein.

The means for passage of electrical connections from the photodiodes to a remote data acquisition system comprises a passageway extending through a portion of one of the housing walls in substantial alignment with the central support section of the housing.

The array of scintillator crystals includes means for fixedly aligning the anti-scatter plates with the non-detecting regions between adjacent crystals. The means for fixedly aligning the anti-scatter plates comprises a recess in each of the non-detecting regions between adjacent crystals. Each of the recesses is adapted to engage a bottom edge of a corresponding anti-scatter plate.

In a preferred embodiment, each of the anti-scatter plates is secured within a portion of a corresponding non-detecting region between adjacent crystals.

The integrated assembly can further include means for fixedly mounting the housing to the frame.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which:

FIG. 3 is a perspective view of a portion of the CT scanner of FIG. 1, in which the integrated assembly of the present invention is shown;

FIG. 4 is a perspective view of a portion of a detector array; and

FIG. 5 is a detail view of a portion of the detector array shown in FIG. 4.

DETAILED DESCRIPTION OF THE INVENTION

Figure 1:
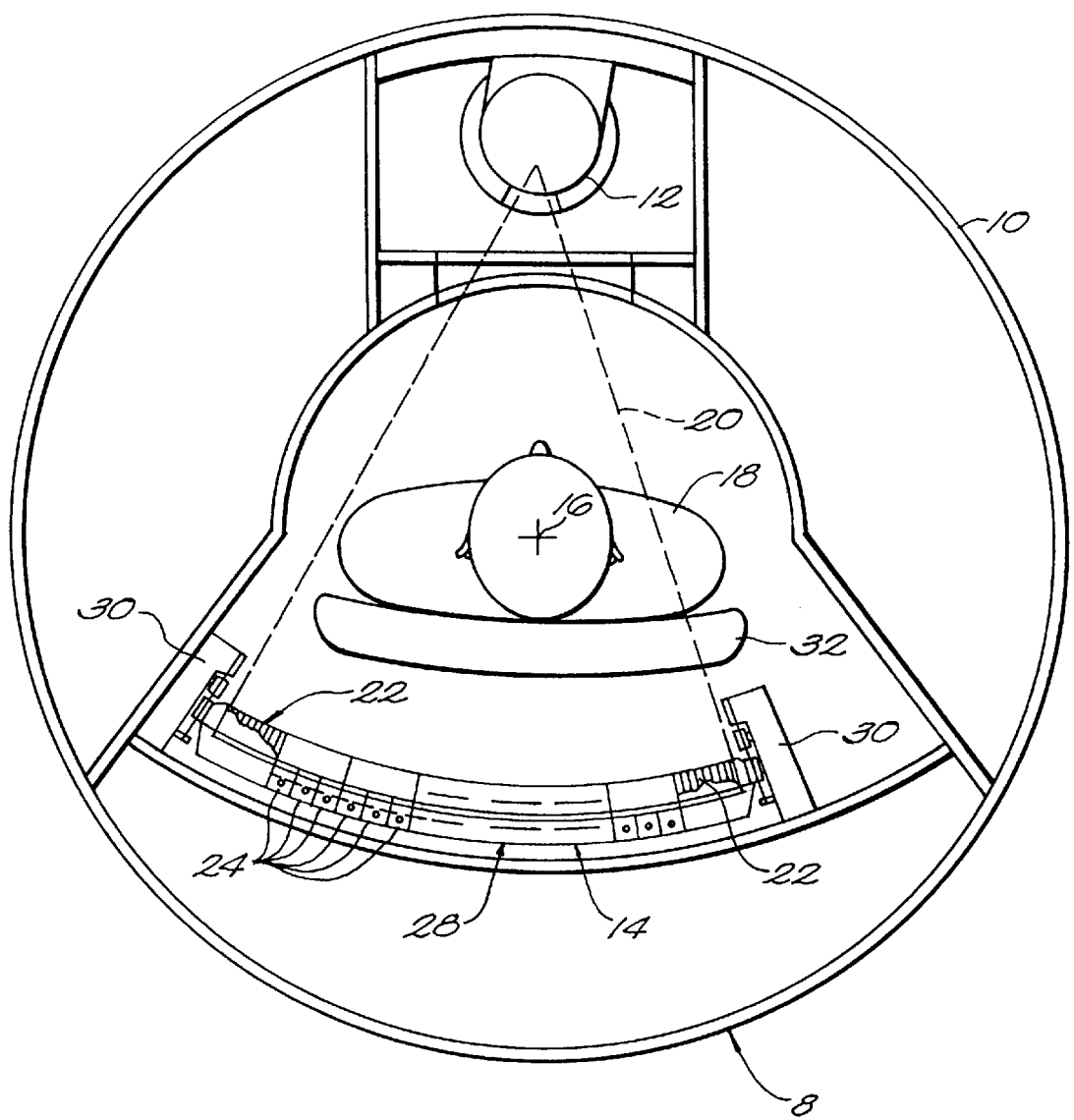
FIG. 1 is an view of a CT scanner including the preferred embodiment of the present invention.

FIG. 1 represents a CT scanner 8 incorporating the principles of the invention. To provide the data for a CT scan, scanner 8 includes a source 12 of X-rays and detector assembly 14 mounted to a disk 10. Source 12 and detector assembly 14 are rotated about rotation axis 16 (extending normal to the view shown in FIG. 1) so as to rotate around the object 18 that extends through the central opening of the disk during the CT scan. Source 12 emits within the scanning plane (normal to rotation axis 16) a continuous fan-shaped beam 20 of X-rays, which are sensed by the detectors of assembly 14 after passing through object 18. The detector/collimator assembly 14 includes an array of scintillator crystals 24 and an array of anti-scatter plates 22. In the preferred embodiment the detectors number between 400 and 700 and cover an arc of approximately 48°. Disk 10, which may advantageously be of a lightweight material, such as aluminum, is caused to rotate around axis 16. The disk 10 is of an open frame construction so that object 18 can be positioned through the opening of the disk. Object 18 may be supported, for example, on a pallet or table 32, which of course, should be as transparent as practical to x-rays. As disk 10 rotates, the detectors of assembly 14 are periodically sampled to provide discrete measurements of x-rays passing in the scanning plane through object 18 from many projection angles. The measurements are then processed electronically with appropriate signal processing equipment (not shown), in accordance with well-known mathematical techniques, so as to produce the final image. The image may then be placed in memory, analyzed in a computer, or suitably displayed.

The detector assembly 14 is mounted to a support element in the form of a supporting reference spine 28, which is supported by disk 10 with suitable supports 30 so that the detectors and collimators all lie in the scanning plane and subtend an equal angle with respect to the focal spot of the X-ray source 12.

Prior to the present invention, great effort has been required to align the detectors and the anti-scatter plates with one another and with their respective support structures to insure proper placement of these components on the rotating disk of a tomography system.

Figure 2:
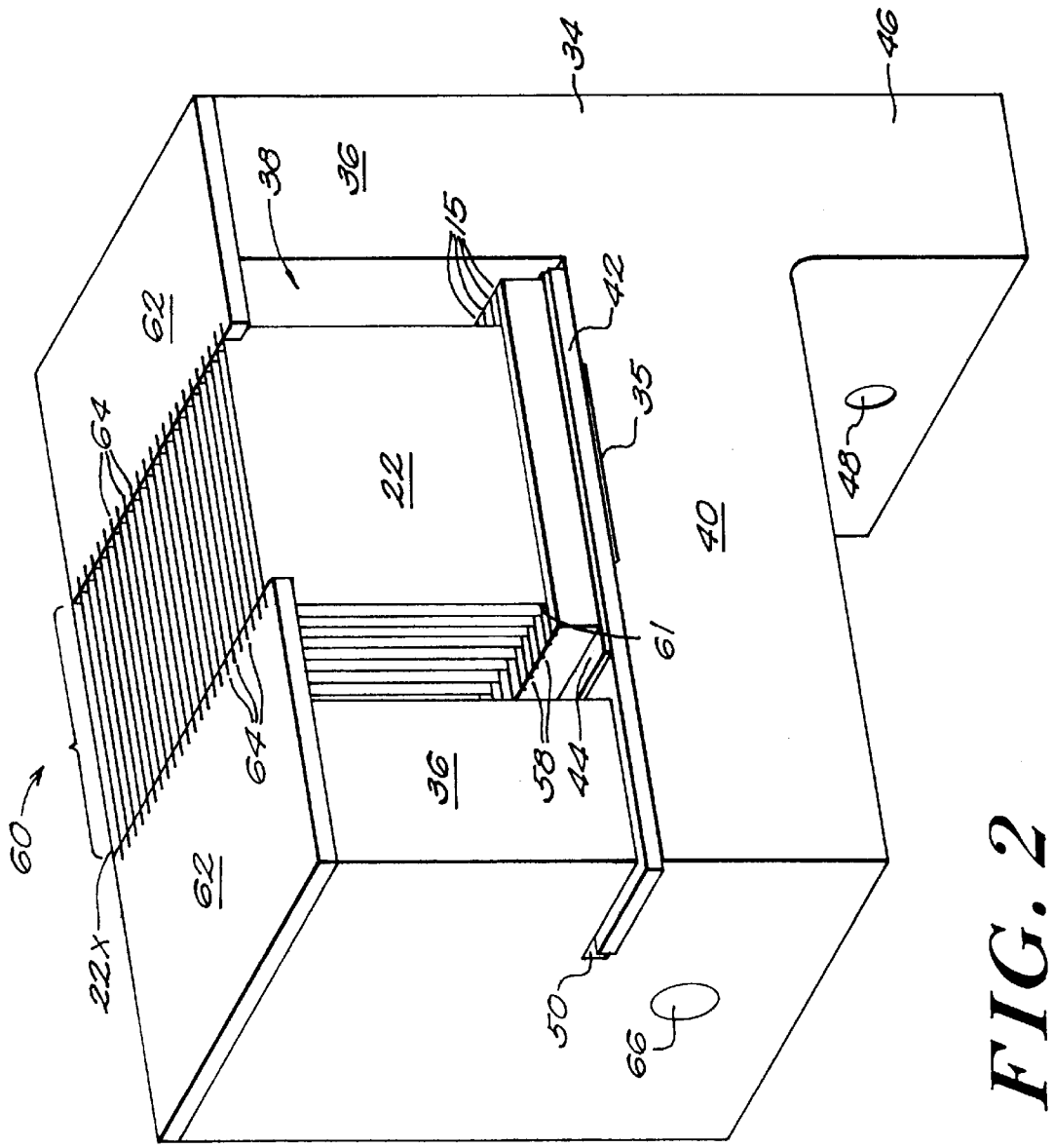
FIG. 2 is a perspective view of an integrated detector and collimator assembly according to the invention.

FIG. 2 illustrates a preferred embodiment of the integrated assembly of the invention. A housing 34 for the detector and anti-scatter plate arrays is in the shape of an inverted chair, as shown clearly in FIGS. 2 and 3. The "legs" of the chair-shaped housing 34 form a pair of walls 36 which extend upward, i.e., radially toward the x-ray source, to provide an interior region 38 within which the detector assembly 14 and anti-scatter plate arrays 22 are located. The "seat" portion of the chair-shaped housing extends horizontally to provide a platform 40 for supporting the substrate 42 on which the photodiodes 44 are mounted. The "back" portion of the chair-shaped housing forms a mounting extension 46 which extends downward and opposite to the direction of extension of the walls 36, i.e., radially away from the radiation source, and includes a precisely located machined hole 48 for a mounting pin for attaching the assembly to, and aligning it with, the spine, as shown in FIG. 3.

Extending along the upper edge of the platform 40 of the housing 34 through one of the walls 36 is a channel or passageway 50 with sufficient clearance to accommodate electronic cabling 51 or other signal transmission lines coupled to the photodiodes, as shown in FIG. 3. This passageway 50 may also provide clearance for a portion of the substrate 42, as shown in FIG. 2. The preferred location for this passageway 50 is through a wall 36 at approximately the same level as the photodiodes 44, so that no strain is induced on the cables from the photodiodes.

A substantially rigid substrate 42, preferably made of ceramic, is positioned and secured on the platform 40 of the housing 34, such as with an adhesive applied in recess 35, as shown in FIG. 2. Preferably a silicone-based adhesive is used for thermal and mechanical stability. An array of photodiodes 44 is arranged on the substrate 42. Electrically conductive leads provide electrical connections between each photodiode and signal transmission means 51.

An array of scintillator crystals 15 is disposed over the photodiode array and arranged so that each crystal 15 is substantially aligned with, and optically coupled to, a corresponding underlying photodiode. Each crystal array preferably includes some 24 individual crystals.

An array of anti-scatter plates 22 is disposed over the scintillator crystals 15 in the ray path and aligned radially with x-rays emanating from the focal spot, so that only radiation arriving at the detectors directly from the focal spot impinges on the faces of the crystals. The anti-scatter plates 22 are preferably made of a substantially x-ray-opaque material, such as tungsten, tantalum or lead, as is known in the art. The anti-scatter plates in the integrated assembly of the present invention are preferably only about 0.1 mm wide and up to about 20 mm in length and width.

As shown in FIG. 4, the scintillator crystals 15 are spaced apart from one another in an array and are separated by relatively narrow non-detecting regions 52. These non-detecting regions 52 include the edges of each individual crystal and any reflective material 54 between adjacent crystals, as detailed more fully below. These non-detecting regions 52 of the crystal array are substantially less sensitive to radiation than the main body of each crystal.

Various schemes have been employed in prior art CT scanner systems in order to minimize the extent of the non-detecting regions in an array of scintillator crystals and therefore maximize the extent of the detecting region. One such scheme provides for an alignment of the anti-scatter plates 22 directly over these non-detecting regions 52 between adjacent crystals so as not to shadow the highly sensitive portions of the crystals. In prior art systems, however, the high resolution demanded in third-generation CT scanners requires a large number of extremely small and closely spaced detector elements. In these systems it has been difficult to maintain the required alignment between the anti-scatter plates and the extremely narrow non-detecting regions between adjacent crystals.

The present invention employs an improvement to the anti-scatter plate alignment scheme to present shadowing of the crystals. According to the invention, each anti-scatter plate 22 is embedded within a portion of a non-detecting region between adjacent scintillator crystals and fixed therein so that their mutual alignment is maintained. Each face of each scintillator crystal, except for the face abutting the underlying photodiode, is coated or covered with an optically reflective coating 54, such as a titanium dioxide paint or epoxy, in order to maximize the reflection of visible light generated by the crystal and transmitted to the photodiode. Each face of each crystal may additionally be covered with a layer of metallic foil or other metallic coating 56 to further enhance internal light reflection and prevent escape of visible light from the crystals in a direction other than toward the photodiodes.

According to a preferred embodiment of the invention, a notch or recess 58 is established in the optically reflective layer or coating 54 or 56 on the upper surface of the crystal array, as illustrated most clearly in FIG. 5. Each notch or recess 58 is located precisely within the confines of a non-detecting region 52 between adjacent crystals, and each recess is sized to receive and engage with a corresponding edge of an anti-scatter plate 22. The depth of the recess is preferably sufficient to engage and hold an edge of an anti-scatter plate, but not so deep as to break through the optically reflective layers 54, 56 to expose any of the underlying crystal surfaces.

If desired, a small amount of a thermally stable adhesive 61 can be applied to the interface between an anti-scatter plate and a corresponding recess to fix the edge of the anti-scatter plate securely in the recess. In this way the anti-scatter plates are fixedly secured relative to the scintillator crystals and aligned with the non-detecting regions between adjacent crystals, so that minimum shadowing of the crystals occurs, even under vibrating or thermally unstable conditions.

Also according to the invention, an x-ray beam collimation region 60 is established between the walls 36 of the housing 34, as previously mentioned and as shown in FIGS. 2 and 3. In a preferred embodiment, the collimation region 60 is defined by a collimation structure 61 which includes a pair of collimator support plates 62. The width of the collimation region 60 is determined by the horizontal separation between the two collimator support plates 62 at the ends of the walls 36. The beam collimation region 60 serves to further focus the x-ray beams incident on the scintillator crystals, thereby minimizing scattered radiation and ensuring that only radiation arriving at the detectors directly from the focal spot reaches the detector crystals.

The collimator support plates 62 include notches or cuts 64 in them, as shown in FIG. 2, which are aligned with one another across the collimation region 60. The notches 64 are sized to receive and engage an edge of a corresponding anti-scatter plate 22 so that the anti-scatter plates can be secured in an appropriate alignment along opposite vertical edges. If desired, a thermally stable adhesive can be applied to the interface between the notches and the edges of the plates to permanently secure the plate edges in the notches.

As shown in FIG. 2, the anti-scatter plate 22x at the rear end of the array is not inserted into slots in the collimator support plates 62 but is instead glued to the edges of the collimation plates 62. This fixation of the end anti-scatter plate 22x against the edges of the collimation structure defines the proper location for the detector assembly 14 and the recesses or slots 64 in the collimator support plates. The anti-scatter plates 22 are secured at the tops of their verticals edges within corresponding slots 64 in the respective collimator support plates, as previously described. The bottom edges of the anti-scatter plates 22 are all aligned with and secured within respective recesses 58 of the detector array over the non-detecting regions 52 between crystals, thereby substantially eliminating further alignment structures or procedures, as well as any x-ray shadowing of the crystals by the anti-scatter plates.

In one embodiment of the invention, the collimator support plates 62 are formed from integral extensions of the walls 36 of the housing and are thus made of the same material as the housing, i.e., aluminum or stainless steel. In this embodiment, an x-ray-opaque covering over the collimator support plates 62 is required in order to define the collimation region 60. In another embodiment, the collimation support plates 62 are separate structures which are secured to the ends of the walls 36, such as with an adhesive. In this latter embodiment the collimator support plates can be made of any substantially x-ray-opaque material, such as, for example, tantalum, tungsten or lead. Tantalum is a preferred material for the collimator support plates 62 because it is opaque to x-radiation and is relatively easy to machine. The selection of materials is governed at least in part by compatibility of thermal expansion characteristics, so that during operation of the scanner the entire assembly contracts and expands uniformly without inducing stresses therein.

The housing 34 is preferably made of a material selected from the group consisting of aluminum and stainless steel.

The platform portion 40 of the chair-shaped housing 34 includes a precisely located machined through hole 66 for a pin or bolt to secure the housing to the spine 28, as shown in FIG. 3. If desired, a spacer 68 can be used between the housing 34 and the spine 28, as shown in FIG. 3.

Although a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. An integrated radiation detecting and collimating assembly for an x-ray tomography system including a source of radiation, means for supporting an object to be scanned, means for detecting radiation passing through said object and for providing electrical signals representative of the relative density of portions of said object, and a frame for rotatably supporting said radiation source and said detecting means relative to said object, said assembly comprising:

a. A plurality of photodiodes arranged in a substantially linear array on a substrate;

b. A plurality of scintillator crystals arranged to receive x-rays from said radiation source, each of said crystals being separated from one another by a substantially non-detecting region, each of said crystals being arranged in an array and aligned and optically coupled with a corresponding photodiode;

c. A plurality of anti-scatter plates arranged over said crystals in a corresponding array, each of said plates being aligned with a corresponding non-detecting region between adjacent crystals; and d. A housing for said assembly, said housing comprising a central support section for supporting said substrate so that said scintillator crystals are exposed to x-rays from said radiation source, and a pair of walls extending from said central support section to define an interior region for said arrays of photodiodes, crystals and anti-scatter plates, and means for passage of electrical connections from said photodiodes through said housing to a remote data acquisition system, wherein said photodiodes, said scintillator crystals and said anti-scatter plates are all fixed relative to one another within said housing, and wherein said housing is adapted for fixation to said frame in a predetermined alignment, and wherein each of said anti-scatter plates is secured within a portion of a corresponding non-detecting region between adjacent crystals, wherein said crystal array includes an optically reflective coating on an upper surface thereof, and wherein each anti-scatter plate is secured within a corresponding recess established in said optically reflective coating and substantially aligned with a corresponding non-detecting region between adjacent crystals of the array.

2. An integrated radiation detecting and collimating assembly according to claim 1 further comprising an x-ray collimation structure extending from said walls to define a radiation collimation region of said housing for receiving and collimating x-rays entering the housing, wherein said x-ray collimation structure includes a pair of collimator support plates and means for aligning and securing said anti-scatter plates between said collimator support plates.

3. An integrated radiation detecting and collimating assembly according to claim 2, wherein said collimator support plates are formed from integral extensions of said walls and include a substantially x-ray-opaque material covering said plates.

4. An integrated radiation detecting and collimating assembly according to claim 3, wherein said x-ray-opaque material is selected from the group consisting of tantalum, tungsten and lead.

5. An integrated radiation detecting and collimating assembly according to claim 2, wherein said collimator support plates are formed from a substantially x-ray-opaque material and are fixedly attached to said walls.

6. An integrated radiation detecting and collimating assembly according to claim 2, wherein said means for aligning and securing said anti-scatter plates between said collimator support plates comprises a plurality of alignment slots in each of said collimator support plates, wherein corresponding alignment slots are aligned with each other and are adapted to engage corresponding edges of an anti-scatter plate therein.

7. An integrated radiation detecting and collimating assembly according to claim 1 further including a passageway extending through a portion of one of said walls and substantially aligned with said central support section wherein said electrical connections pass through said passageway.

8. An integrated radiation detecting and collimating assembly for an x-ray tomography system, comprising:
   a. a plurality of photodiodes arranged in an array;
   b. a plurality of scintillator crystals arranged in an array, wherein each set of adjacent crystals is separated by a substantially non-detecting region, and each crystal is aligned and optically coupled with a corresponding photodiode;
   c. an optically reflective coating disposed on the crystals so as to form recesses over the non-detecting regions and so as to transmit X-rays through the coating into each of said crystals ad reflect light emitted by said crystals toward said photodiodes;
   d. a plurality of anti-scatter plates arranged over said crystals in a corresponding array, each of said plates being aligned with a corresponding non-detecting region between adjacent crystals; and
   e. a housing for supporting said diodes, scintillator crystals and anti-scatter plates so that they are fixed relative to one another and in proper alignment when the housing is secured to the X-ray tomography system;

wherein each of said anti-scatter plates is aligned with a portion of a corresponding non-detecting region between adjacent crystals and secured within a corresponding recess established in said optically reflective coating.

9. An integrated radiation detecting and collimating assembly according to claim 8, further comprising a thermally stable adhesive applied to at least one of the recess and a bottom edge of a corresponding anti-scatter plate.

10. An integrated radiation detecting and collimating assembly according to claim 8, further comprising an x-ray collimation structure extending from said walls to define a radiation collimation region of said housing for receiving and collimating x-rays entering the housing, wherein said x-ray collimation structure includes a pair of collimator support plates and support structure for aligning and securing said anti-scatter plates between said collimator support plates.

11. An integrated radiation detecting and collimating assembly according to claim 10, wherein said collimator support plates are formed from integral extensions of said walls and include a substantially x-ray-opaque material covering said collimator support plates.

12. An integrated radiation detecting and collimating assembly according to claim 11, wherein said x-ray-opaque material is selected from the group consisting of tantalum, tungsten and lead.

13. An integrated radiation detecting and collimating assembly according to claim 10, wherein said collimator support plates are formed from a substantially x-ray-opaque material and are fixedly attached to said walls.

14. An integrated radiation detecting and collimating assembly according to claim 10, wherein said means for aligning and securing said anti-scatter plates between said collimator support plates comprises a plurality of alignment slots in each of said collimator support plates, wherein corresponding alignment slots are aligned with each other and are adapted to engage corresponding edges of an anti-scatter plate therein.

15. An X-ray tomography system comprising an X-ray source supported on a rotatable disk, and the integrated radiation detecting and collimating assembly as defined in claim 8.

16. An X-ray tomography system according to claim 15 wherein the integrated radiation detecting and collimating assembly is supported on said rotatable disk and aligned with said X-ray source.

* * * * *